United States Patent
Raulerson et al.

(10) Patent No.: US 7,329,248 B2
(45) Date of Patent: Feb. 12, 2008

(54) CATHETER SHEATH PINCH CLAMP

(75) Inventors: J. Daniel Raulerson, Brewton, AL (US); Earl Voorhees, Warrington, PA (US); John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 372 days.

(21) Appl. No.: 10/781,119

(22) Filed: Feb. 18, 2004

(65) Prior Publication Data
US 2004/0186445 A1 Sep. 23, 2004

Related U.S. Application Data

(60) Provisional application No. 60/461,364, filed on Apr. 9, 2003, provisional application No. 60/448,206, filed on Feb. 18, 2003.

(51) Int. Cl.
*A61M 25/00* (2006.01)
(52) U.S. Cl. .................. 604/523; 604/160; 604/161; 604/162; 604/264; 604/355
(58) Field of Classification Search ............. 604/523, 604/160, 161, 162, 264
See application file for complete search history.

(56) References Cited

U.S. PATENT DOCUMENTS

| 4,526,172 | A | * | 7/1985 | Stephenson ............... 606/208 |
| D283,918 | S | | 5/1986 | Jacobson |
| 4,586,691 | A | | 5/1986 | Kozlow |
| 4,589,171 | A | | 5/1986 | McGill |
| 4,596,559 | A | * | 6/1986 | Fleischhacker ........ 604/164.05 |
| 4,643,389 | A | | 2/1987 | Elson et al. |
| 5,207,649 | A | | 5/1993 | Aruny |
| 5,238,218 | A | | 8/1993 | Mackal |
| 5,261,416 | A | | 11/1993 | Taussig |
| 5,318,546 | A | | 6/1994 | Bierman |
| 5,401,256 | A | | 3/1995 | Stone et al. |
| D362,062 | S | | 9/1995 | Botts et al. |
| 5,453,098 | A | | 9/1995 | Botts et al. |
| 6,117,115 | A | | 9/2000 | Hill et al. |
| 6,213,988 | B1 | * | 4/2001 | McIvor et al. ............. 604/264 |
| 6,364,279 | B1 | | 4/2002 | Neftel et al. |
| 2001/0021824 | A1 | | 9/2001 | Marsh et al. |

* cited by examiner

*Primary Examiner*—Kevin C. Sirmons
*Assistant Examiner*—Phillip Gray
(74) *Attorney, Agent, or Firm*—Anton P. Ness; Fox Rothschild LLP

(57) ABSTRACT

A catheter insertion sheath assembly (100) including a tubular sheath body (106) having a proximal end (102), a distal end (104), and a hollow passage (107) extending between the proximal end and the distal end. A handle portion (110,114) is disposed at the proximal end of the tubular sheath. A clamp (120;300;400) extends from the handle portion for releasably closing the sheath prior to insertion of a catheter thereinto and includes a relatively movable portion (130) or portions (310,310';410,410') that is or are movable between an open position and a closed position, wherein, when the clamp is in the open position, fluid may flow through the hollow passage between the proximal end and the distal end and when the clamp is in the closed position, fluid flow is restricted through the hollow passage between the proximal end and the distal end.

14 Claims, 7 Drawing Sheets

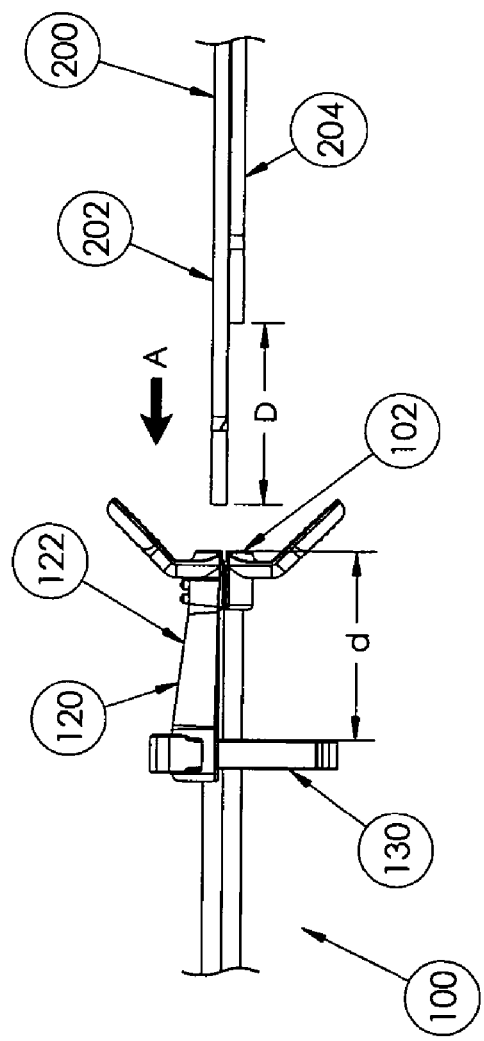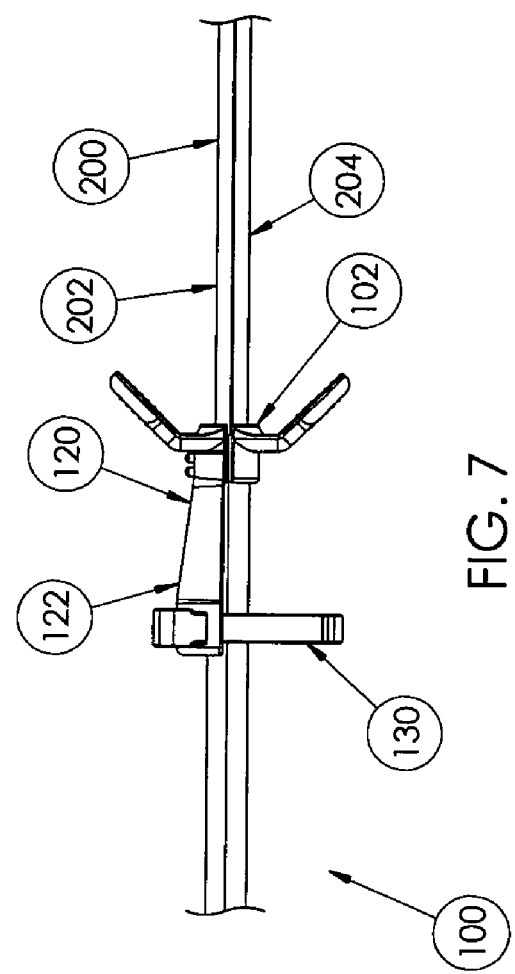

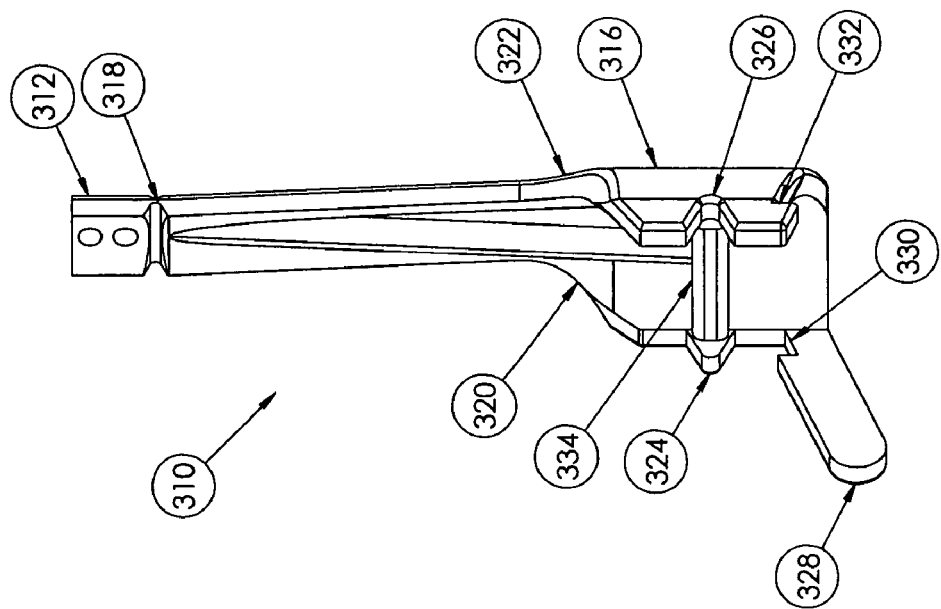
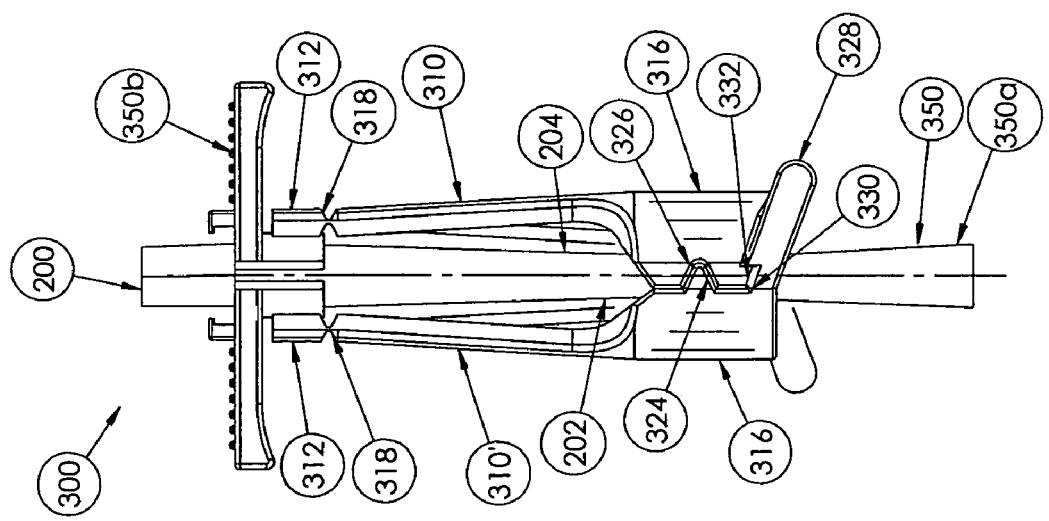
FIG. 9
FIG. 8

CATHETER SHEATH PINCH CLAMP

CROSS-REFERENCE TO RELATED APPLICATIONS

This application claims the benefit of U.S. Provisional Application Ser. No. 60/448,206, filed Feb. 18, 2003 and U.S. Provisional Application Ser. No. 60/461,364, filed Apr. 9, 2003.

FIELD OF THE INVENTION

The present invention relates to a clamp and a method for preventing blood from flowing from a catheter introducer sheath and for preventing an air embolism from being drawn into the catheter introducer sheath during catheter installation.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter in which one lumen introduces fluid and the other lumen removes fluid. An example of such a multiple lumen catheter is the SPLIT CATH® catheter, sold by Medical Components, Inc. of Harleysville, Pa. Catheterization may also be performed by using a multiple lumen assembly consisting of separate, single lumen catheters inserted through one or two different incisions into an area to be catheterized. An example of such a multiple lumen assembly is the TESIO® catheter, also sold by Medical Components, Inc.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device and the guide wire are then removed, leaving the end portion of the guide wire that has been inserted into the vessel within the vessel and the opposing end of the guide wire projecting beyond the surface of the skin of the patient.

At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire. For example, this technique may be used to insert small diameter dual lumen catheters into a patient. If the catheter to be inserted is significantly larger than the guide wire, a sheath with a dilator device is passed over the guide wire to enlarge the hole. After the hole is sufficiently enlarged, the dilator and the guide wire are removed, leaving the sheath. The catheter is then inserted into the sheath. The sheath is torn and removed from around the exterior or the catheter.

However, after the dilator is removed, and before the catheter is inserted through the sheath, the sheath becomes an open conduit, allowing blood to spurt from the vessel through the sheath or allowing air to be aspirated into vessel through the sheath, such as when the patient draws a deep breath. It would be beneficial to provide a clamp that clamps off the sheath after the dilator is removed, preventing blood from spurting out the sheath or preventing air from being aspirated in prior to inserting the catheter. It would be further beneficial to provide a clamp that can be closed and opened using only one hand, so that the physician inserting the catheter still has a free hand with which to work.

BRIEF SUMMARY OF THE INVENTION

Briefly, the present invention provides a catheter insertion sheath comprising a tubular sheath having a proximal end, a distal end, and a hollow passage extending between the proximal end and the distal end. The sheath also includes a handle portion disposed at the proximal end of the tubular sheath and means extending from the handle portion for releasably closing the sheath. The means are movable between an open position and a closed position. When the means are in the open position, fluid may flow through the hollow passage between the proximal end and the distal end and when the means are in the closed position, fluid flow is restricted through the hollow passage between the proximal end and the distal end.

The present invention also provides a catheter insertion sheath comprising a flexible elongated body having a proximal end, a distal end, and a longitudinal axis extending therethrough. The sheath also includes a handle connected to the proximal end of the body and a pinching member for pinching the body closed. The pinching member extends from the handle and wherein the pinching member is operable between and open position and a closed position.

Also, the present invention provides a catheter sheath assembly comprising a catheter sheath including a generally tubular sheath body having a proximal end and a distal end and a handle fixedly connected to the proximal end of the sheath body. The assembly also includes a catheter sheath clamp assembly comprising a body having a first end connected to the sheath handle and a second end having a slot extending through the body, and a generally planar pinch member slidingly disposed within the slot transversely with respect to the tubular sheath body to be translated between an open position and a pinching position. The pinch member includes a first pinch leg having a first tapered free end and a first connected end and a second pinch leg juxtaposed from the first pinch leg. The second pinch leg has a second tapered free end and a second connected end connected to the first connected end. The pinch member is slidable transversely within the slot between a first or open position wherein the first and second tapered free ends are proximate to the slot and a second or closed position wherein the first and second connected ends are proximate to the slot and the first and second pinch legs compress the tubular sheath body closed.

The present invention further provides a method of operating a pinch clamp for releasably pinching off fluid flow through a catheter insertion sheath. The method comprises providing a clamp over a catheter insertion sheath, wherein the catheter insertion sheath includes a longitudinal axis extending therethrough; using a thumb on one hand to bias a first engagement portion of the clamp toward the longitudinal axis; and using at least one finger on the hand to bias a second engagement portion of the clamp toward the longitudinal axis, such that the first engagement portion releasably engages the second engagement portion and the flexible conduit is pinched off by the first engagement portion and the second engagement portion.

The present invention also provides a method of inserting a catheter into a catheter sheath, wherein the catheter sheath comprises a proximal end, a distal end and a sheath clamp disposed proximate to the proximal end. The method comprises inserting a catheter sheath into a blood vessel of a patient; securing the sheath clamp to the sheath to restrict fluid flow between the proximal end and the distal end of the sheath; inserting a catheter into the proximal end of the sheath and advancing the catheter toward the sheath clamp; releasing the sheath clamp from the sheath; advancing the catheter through the sheath to the distal end of the sheath; and removing the sheath from the blood vessel.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 6 is a side elevational view of a catheter being inserted into the catheter sheath with the sheath clamp of FIG. 1.

FIG. 7 is a side elevational view of the catheter of FIG. 6 having been inserted into the catheter sheath with the sheath clamp of FIG. 1.

FIG. 8 is a perspective view of a catheter sheath clamp assembly constructed in accordance with a second embodiment of the present invention, with the clamp in a closed position.

FIG. 9 is a perspective view of a clamp segment of the catheter sheath clamp assembly of FIG. 8.

DETAILED DESCRIPTION OF THE PRESENT INVENTION

Figure 2:
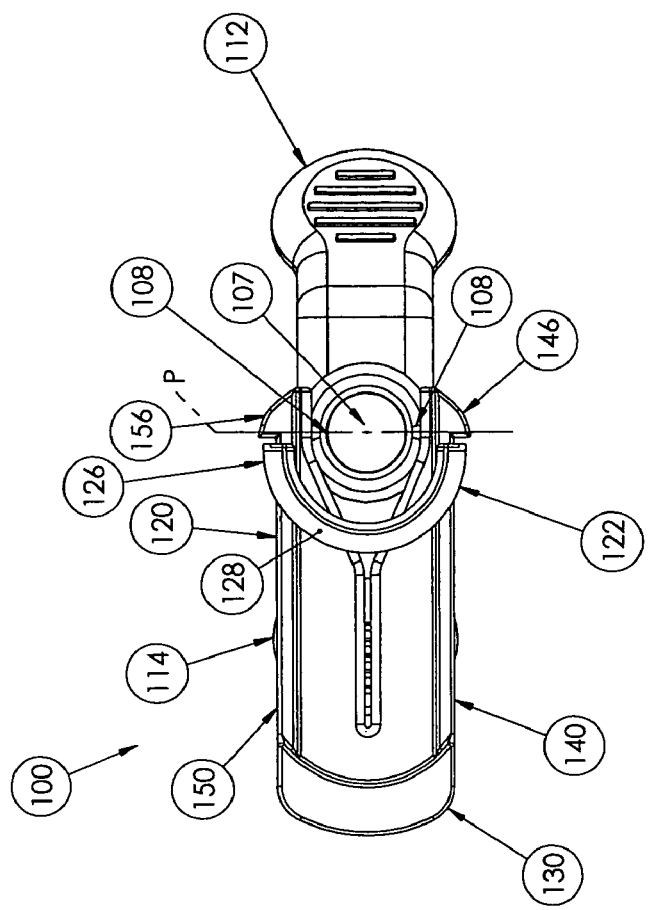
FIG. 2 is an enlarged bottom plan view of the catheter sheath with the sheath clamp, taken along lines and arrows 2-2 in FIG. 1.

In the drawings, like numerals indicate like elements throughout. Certain terminology is used herein for convenience only and is not to be taken as a limitation on the present invention. The words "proximal" and "distal" refer to directions away from and closer to, respectively, the insertion tip of a catheter insertion sheath incorporating a sheath clamp according to the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

Figure 1:
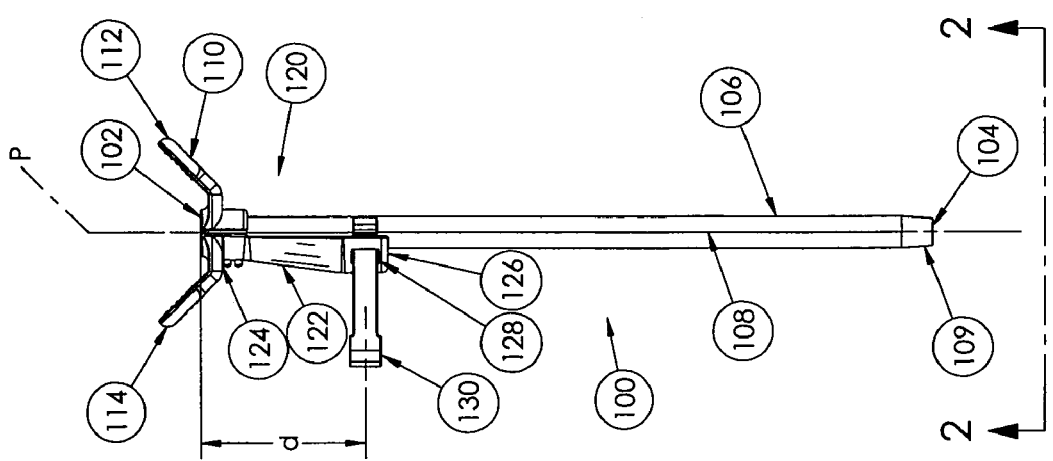
FIG. 1 is a side elevational view of a catheter sheath with a sheath clamp according to a first embodiment of the present invention, with the sheath clamp in an "open" position.

Referring to FIGS. 1 and 2, a catheter sheath 100 incorporating a sheath clamp 120 according to a first embodiment of the present invention is shown. The catheter sheath 100 is used during insertion of a catheter into a blood vessel in a patient to assist the inserting physician in inserting the catheter into the vessel. The sheath 100 is typically inserted mounted on a dilator (not shown) and the sheath 100 and dilator are inserted into the blood vessel prior to insertion of the catheter into the blood vessel, as is well known in the art. The dilator and sheath 100 expand the opening into the blood vessel to allow the catheter to be inserted into the opening. After the opening into the blood vessel is expanded, the dilator is removed, leaving the sheath 100 in place. A catheter is inserted into the sheath 100 and into the blood vessel.

The catheter sheath 100 includes a proximal end 102, a distal end 104, and an elongated, generally cylindrical sheath body 106 extending between the proximal end 102 and the distal end 104. The sheath body 106 includes a generally cylindrical passageway 107 that extends through the body 106 between the proximal end 102 and the distal end 104. The passageway 107 is sized to allow the dilator (not shown) to be inserted through the sheath body 106 from the proximal end 102 of the sheath 100 to the distal end 104 of the sheath 100 such that the dilator engages the sheath body 106 surrounding the passageway 107 in a slight frictional fit.

The sheath body 106 further includes a pair of diametrically opposed tear seams 108 that extend between the proximal end 102 of the sheath 100 and the distal end 104 of the sheath 100. A plane P that includes both of the tear seams 108 extends perpendicularly from the plane of the paper of FIG. 1. The sheath body 106 is flexible to allow the sheath body 106 to be compressed into the passageway 107, restricting fluid communication between the proximal end 102 of the sheath 100 and the distal end 104 of the sheath 100. Preferably, the sheath body 106 is constructed from high density polyethylene, although those skilled in the art will recognize that the sheath body 106 may be constructed from some other suitable, biocompatible flexible material.

The distal end 104 of the sheath 100 includes a generally frusto-conical distal tip 109 that provides a smooth transition from the dilator that is inserted through the distal end 104 of the sheath 100 to the sheath body 106, to facilitate insertion of the dilator and sheath 100 together into the blood vessel in the patient.

The proximal end 102 of the sheath 100 includes a handle 110 that connects with the sheath body 106 to form generally a "T" shape. The handle 110 includes a first handle portion 112 that extends from the sheath body 106 wholly on one side of the plane P and a second handle portion 114 that extends from the sheath body 106 wholly on an opposing side of the plane P.

The second handle portion 114 includes the sheath clamp 120 extending therefrom toward the distal end 104 of the sheath 100. The sheath clamp 120 includes a preferably generally elongated body 122 having a connected end 124 that is fixed to the second handle portion 114 and a free end 126 that is located distally of the second handle portion 114. The body 122 is generally concave in lateral cross-section, and extends only along one side of the plane P. As can be seen from either of FIGS. 1 or 2, the body 122 is on the left side of the plane P. The body 122 may be manufactured concurrently as part of the handle 110, or the body 122 may be formed separately from the handle 110, and later connected to the handle 110 by methods known to those skilled in the art, such as by ultrasonic welding, or other suitable method.

The body 122 includes a slot 128 proximate to the free end 126 of the body 122. The slot 128 extends generally perpendicular to the plane P. A generally planar pinch member 130 extends through the slot 128 transversely with respect to the tubular sheath body 106, to releasably pinch the sheath body 106, restricting fluid flow between the proximal end 102 of the sheath body 106 and the distal end 104 of the sheath body 106.

Figure 3:
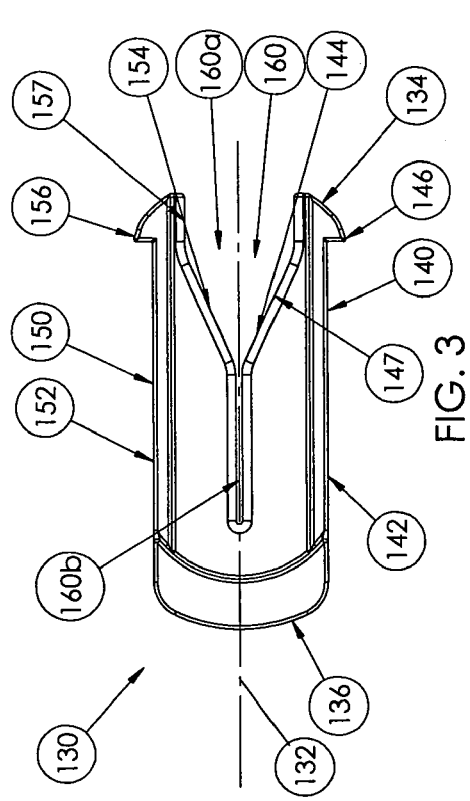
FIG. 3 is a top plan view of a pinch member used in the catheter sheath with a sheath clamp shown in FIGS. 1 and 2.

A planar view of the pinch member 130 is shown in FIG. 3. The pinch member 130 includes a centerline 132 that extends between a free end 134 of the pinch member 130 and a connected end 136 of the pinch member 130. The pinch member 130 further includes a first leg 140 and a second leg 150 that each extend on either side of the centerline 132 from the connected end 136 toward the free end 134.

The first leg 140 includes a first longitudinal side 142 and a second longitudinal side 144. The second longitudinal side 144 extends generally parallel to the first longitudinal side 142 for a predetermined length from the connected end 136, then tapers away from the centerline 132 toward the free end 134 of the pinch member 130. A retainer nub 146 extends away from the first longitudinal side 142 of the first leg 140 proximate to the free end 134 of the pinch member 130. A first rib 147 extends along the second longitudinal side 144 toward the second leg 150.

The second leg 150 is preferably a mirror image of the first leg 140 across the centerline 132. The second leg includes a first longitudinal side 152 and a second longitudinal side 154. The second longitudinal side 154 extends generally parallel to the first longitudinal side 152 for a predetermined length from the connected end 136, then tapers away from the centerline 132 toward the free end 134 of the pinch member 130. A retainer nub 156 extends away from the first longitudinal side 152 of the second leg 150 proximate to the free end 134 of the pinch member 130. A second rib 157 extends along the second longitudinal side 154 toward the first leg 140.

A channel 160 is formed along the centerline 132 between the second longitudinal side 144 of the first leg 140 and the second longitudinal side 154 of the second leg 150. The channel 160 is generally funnel-shaped, with a wider portion 160a proximate to the free end 134 of the pinch member 130 and a narrow, generally straight portion 160b proximate to the connected end 136 of the pinch member 130.

As can be seen in FIGS. 1 and 2, the pinch member 130 extends through the slot 128 in the clamp body 122 generally perpendicular to the plane P.

When the clamp 120 is in an open position, as shown in FIGS. 1 and 2, the pinch member 130 is retained within the slot 128 by the nubs 146, 156, which each engage the body 122. The nubs 146, 156 prevent the pinch member 130 from being pulled out of the slot 128 from right to left as shown in FIG. 1. With the pinch member 130 in this position, the sheath body 106 is disposed in the wider portion 160a of the channel 160 and is in an open position, allowing for fluid communication between the proximal end 102 of the sheath 100 and the distal end 104 of the sheath 100.

The pinch member 130 is preferably constructed from polypropylene, or any other suitable material that has memory. By "memory", it is meant that the material, when biased away from a rest position, tends to return toward the rest position when the material is released from the biased position.

Figure 4:
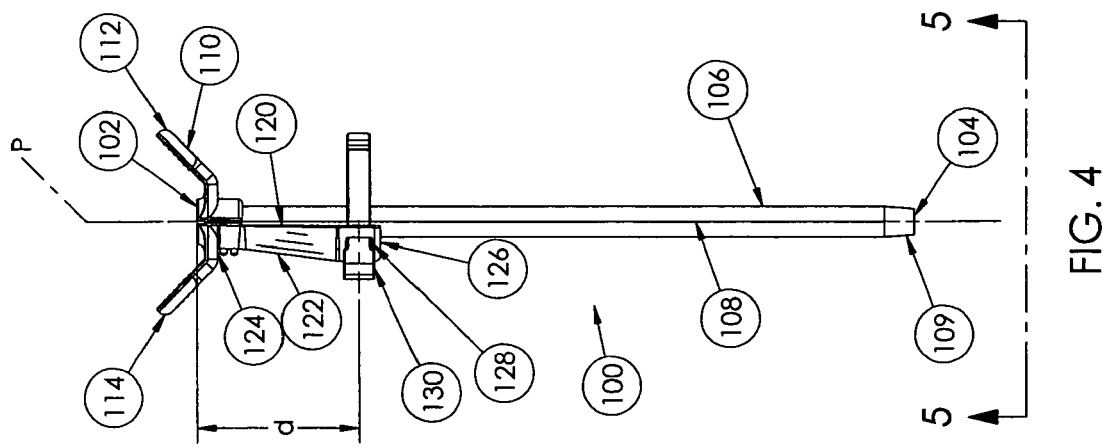
FIG. 4 is a side elevational view of a catheter sheath with a sheath clamp according to a first embodiment of the present invention, with the sheath clamp in an "closed" position.
Figure 5:
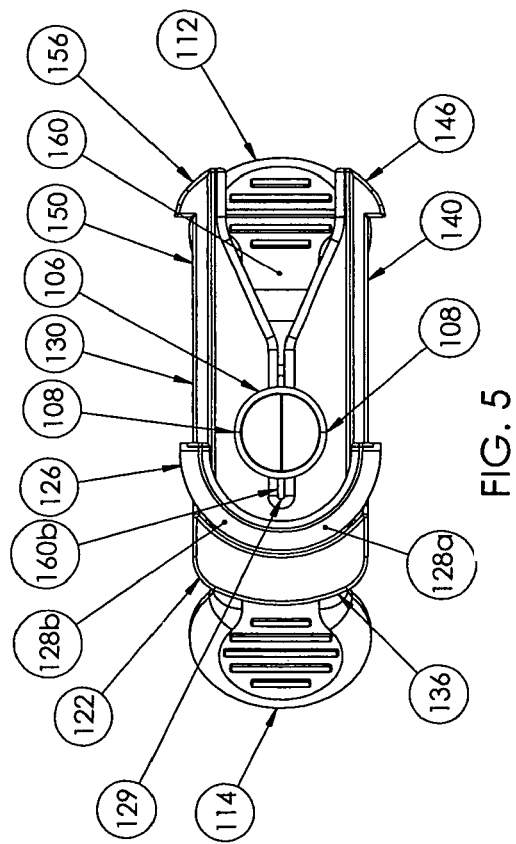
FIG. 5 is a side elevational view of the catheter of FIG. 4, having been partially inserted into the catheter sheath with sheath clamp.

When the clamp 120 is moved to a closed position, by moving the pinch member 130 from left to right, from the position shown in FIGS. 1 and 2 to the position shown in FIGS. 4 and 5, the pinch member 130 is retained within the slot 128 by the sheath 120. In this position, the sheath body 106 is disposed in the narrower portion 160b of the channel 160 and is pinched closed by the clamp 130, restricting fluid communication between the proximal end 102 of the sheath 100 and the distal end 104 of the sheath 100, either in the form of blood flowing from the distal end 104 of the sheath 100 toward the proximal end 102 of the sheath 100 or air flowing from the proximal end 102 of the sheath 100 toward the distal end 104 of the sheath 100. The first and second ribs 147, 157 provide narrow points of contact between the pinch member 130 and the sheath 100, increasing pressure between the pinch member 130 and the sheath 100, thereby magnifying the ability of the pinch member 130 to restrict fluid flow through the sheath 100.

As the pinch member 130 is slid from left to right, as shown from FIG. 1 to FIG. 4, the sheath body 106 is directed by the wider portion 160a of the channel 160 toward the narrower portion 160b of the channel 160. As the sheath body 106 is forced into the narrower portion 160b of the channel 160, the sheath body 106 forces the first and second legs 140, 150, respectively, compress the sheath body 106 into the passageway 107. The memory of the material from which the pinch member 130 is constructed forces the first and second legs 140, 150 at the free end 134 of the pinch member 130 toward each other, so that the sheath body 106 remains compressed into the passageway 107 between the second longitudinal side 144 of the first leg 140 and the second longitudinal side 154 of the second leg 150.

In operation, the sheath 100, with a dilator (not shown) inserted through the passageway 107 in the sheath body 106, is inserted over a guide wire (not shown) during insertion of a catheter into a blood vessel of a patient, preferably using techniques known to those skilled in the art. At this time, the sheath clamp 120 is in the open position, as shown in FIG. 1. After the sheath 100 and dilator are properly inserted, the guide wire and the dilator are then removed by pulling the guide wire, and then the dilator, proximally through the sheath 100. As the dilator clears the plane of the pinch member 130, the sheath clamp 120 is closed by sliding the pinch member 130 from left to right, as shown from FIG. 1 to FIG. 4. Preferably, the inserting physician is able to grasp the sheath body 106 with several fingers of one hand and, using the same hand, place his thumb on the connected end 136 of the pinch member 130. The physician uses the thumb to slide the pinch member 130 from left to right, from the position shown in FIG. 1 to the position shown in FIG. 4.

Referring now to FIG. 6, the preferably elongated body 122 of the sheath clamp 120 allows the pinch member 130 to be disposed a distance "d" from the proximal end 102 of the sheath 100. The distance "d" allows a catheter, such as the catheter 200 shown in FIG. 6, having a first lumen 202 and a second lumen 204 with differing lengths, with a distance "D" separating the distal tip of the first lumen 200 from the distal tip of the second lumen 204, such as a SPLIT CATH® catheter, to be inserted into the sheath 100 while the pinch member 130 is in a closed position, as shown in FIG. 6, allowing the inserting physician to insert the first and second lumens 202, 204 into the sheath 100, as shown in FIG. 7, without the patient's blood flowing from the proximal end 102 of the sheath 100. Preferably, the distance "d" is at least as great as the distance "D", so that the distal tips of both lumens 202, 204 may be inserted into the sheath 100 while the pinch member 130 is in a closed position. In catheter 200. the first lumen 202 is longer than the second lumen 204 to reduce recirculation of the patient's blood during hemodialysis.

Since the first lumen 202 is longer than the second lumen 204 by the distance "D", the first lumen 202 must be inserted the distance "D" into the proximal end 102 of the sheath 100 until the second lumen 204 enters the proximal end 102 of the sheath 100. In this manner, the first and second lumens 202, 204 generally occlude the passageway 107 and restrict the flow of blood from the vessel and through the sheath 100 when the pinch member 130 is moved to the open position.

The pinch member 130 is next slid from the closed position shown in FIG. 4 to the open position shown in FIG. 1, but with the catheter 200 partially inserted into the sheath 100. Preferably, the inserting physician is able to grasp the sheath body 106 with several fingers of one hand and, using the same hand, place his thumb on the free end 134 of the pinch member 130. The physician uses the thumb to slide the pinch member 130 from right to left, as shown from FIG. 4 to FIG. 1.

After the pinch member 130 is slid to the open position, the catheter lumens 202, 204 are further inserted into the sheath 100 until the catheter 200 is placed in a desired location in the patient. The inserting physician then grasps each of the first and second handle portions 112, 114 and pulls them apart from each other, tearing the sheath 100 along the tear seams 108 from the proximal end 102 of the sheath 100 toward the distal end 104 of the sheath 100. As the sheath 100 is being torn, the sheath 100 is being pulled out of the patient. The sheath 100 is torn along the tear seams 108 until the sheath 100 is fully torn to the distal end 104 of the sheath 100 and removed. The sheath 100, now removed from the patient and in two separate pieces, is then discarded and the catheter 100 is further inserted into the patient according to known methods.

While the catheter 200 shown in FIGS. 6 and 7 is a split-tip catheter having lumens 202, 204 of differing lengths, those skilled in the art will recognize that other types of catheters, including single lumen catheters, such as the TESIG® catheter, may also be used with the sheath 100 and clamp 120 without departing from the scope of the present invention.

Referring now to FIGS. 8 and 9, a sheath clamp 300 according to a second embodiment of the present invention is shown. The clamp 300 is used to releasably clamp a conduit, such as a catheter introducer sheath 350. The sheath 350 has a distal end 350a that is inserted into a patient's blood vessel during catheter insertion, and a proximal end 350b that remains outside the patient.

The sheath 350 is preferably generally identical to the sheath 100 described above. The clamp 300 is bonded to the sheath 350 preferably in the same manner as the clamp 120 is bonded to the sheath 100, also described above. Referring to FIG. 9, the clamp 300 includes a first clamping segment 310 having a top portion 312 that is fixedly connected to the proximal end 350b of the sheath 350.

The first clamping segment 310 further includes a body portion 316 that is preferably connected to the top portion 312 by a living hinge 318. The body portion 316 further includes a first side portion 320 and a second side portion 322. The body portion 316 is generally concave between the first and second side portion 320, 322, although those skilled in the art will recognize that the body portion 316 may be generally planar, or some other shape as well.

The first side portion 320 includes a generally triangular tongue or first tab 324 that extends therefrom, generally perpendicular to a plane of the body portion 316. The second side portion 322 includes a complementary groove or first recess 326 that is sized and shaped to fittingly engage a tongue 324 from a second clamping segment 310', as shown in FIG. 8.

Referring still to FIG. 9, a locking leg 328 extends from the first side portion 320 distal from the top portion 312. Preferably, the locking leg 328 is generally co-planar with the tongue 324. A recessed portion or second recess 330 is disposed on the first side portion 320 proximate to the locking leg 328. The recessed portion 330 is disposed generally along the locking leg 328. The second side portion 322 includes a complementary tang or second tab 332 that is sized and shaped to fittingly engage a recessed portion 330 from the second clamping segment 310', as shown in FIG. 8.

Although, as shown in FIGS. 8 and 9, the tongue 324, the locking leg 328, and the recessed portion 330 are all disposed along the first side portion 320 and the groove 326 and the tang 332 are both disposed along the second side portion 322, those skilled in the art will recognize that the tongue 324, the groove 326, the locking leg 328, the recessed portion 330 and the tang 332 may be disposed along either the first side portion 320 or the second side portion 322, so long as the tongue 324 and the groove 326 are disposed along different side portions, and the recessed portion 330 and the tang 332 are disposed along different side portions.

The first clamping segment 310 further includes a clamping member 334 disposed between the first and second side portions 320, 322, respectively. As seen in FIG. 9, the clamping member 334 preferably extends generally along a plane defined by the tongue 324 and the groove 326, although those skilled in the art will recognize that the clamping member 334 may be disposed generally above or below this plane instead.

The second clamping segment 310' is preferably, although not necessarily, generally identical to the first clamping segment 310. For example, comparing the first clamping segment 310 shown in FIG. 9 to a similar, but non-identical clamping segment 310' in FIG. 10, while the first clamping segment 310 includes one clamping member 334, the second clamping segment 310' may have two clamping members 334a, 334b, such that, when the clamp 300 is in a closed position, as shown in FIG. 8, clamping member 334 is disposed generally between clamping members 334a, 334b.

The clamp 300 is used to restrict fluid flow through the sheath 350 by engaging the first clamping segment 310 and the second clamping segment 310' with each other. Prior to operating the clamp 300, the sheath 350 is inserted into a patient during catheter insertion to facilitate insertion of the catheter lumens 202, 204, shown in FIG. 8, into the blood vessel being catheterized. Initially, the clamp 300 is in the open condition. The distal end 350a of the sheath 350, with a dilator (not shown) is inserted into the blood vessel over a guide wire (not shown) according to known techniques, while the proximal end 350b of the sheath 350 remains outside the patient, so that the catheter 200 can be inserted through the proximal end 350b of the sheath 350 and into the blood vessel. After insertion of the dilator and sheath 350 over the guide wire, the guide wire is removed by pulling the guide wire proximally through the dilator. The dilator is then removed from the sheath 350 by pulling the dilator proximally from the sheath 350.

After removing the dilator from the sheath 350 and prior to inserting the catheter into the sheath 350, the inserting physician secures the clamp 300 to the position shown in FIG. 8, preventing blood loss and air aspiration at the proximal end 350*b* of the sheath 350. The physician uses the thumb of one hand to bias the body portion 316 of the first clamping segment 310 toward the sheath 350 and a finger on the same hand to bias the body portion 316 of the second clamping segment 310' toward the sheath 350. The first and second clamping segments 310, 310' each pivot about their respective living hinges 318 toward the sheath 350.

The tongue 324 of the first clamping segment 310 enters the groove 326 of the second clamping segment 310' and the tongue 324 of the second clamping segment 310' enters the groove 326 of the first clamping segment 310 so that the first and second clamping segments 310, 310' are properly aligned with each other. The tang 332 of the first clamping segment 310 engages the top of the locking leg 328 on the second clamping segment 310', biasing the locking leg 328 downward, away from the tongue 324. The tang 332 then snaps into the recessed portion 330 of the second clamping segment 310' and the locking leg 328 returns toward its unbiased position.

Simultaneously, the tang 332 of the second clamping segment 310' engages the top of the locking leg 328 on the first clamping segment 310, biasing the locking leg 328 downward, away from the tongue 324. The tang 332 then snaps into the recessed portion 330 of the first clamping segment 310 and the locking leg 328 returns toward its unbiased position. The tongue 324 and the recess 326 serve primarily as alignment tools, while the locking of the first clamping segment 310 and the second clamping segment 310' to each other is performed by the tang 332 and the recessed portion 330.

Figure 10:
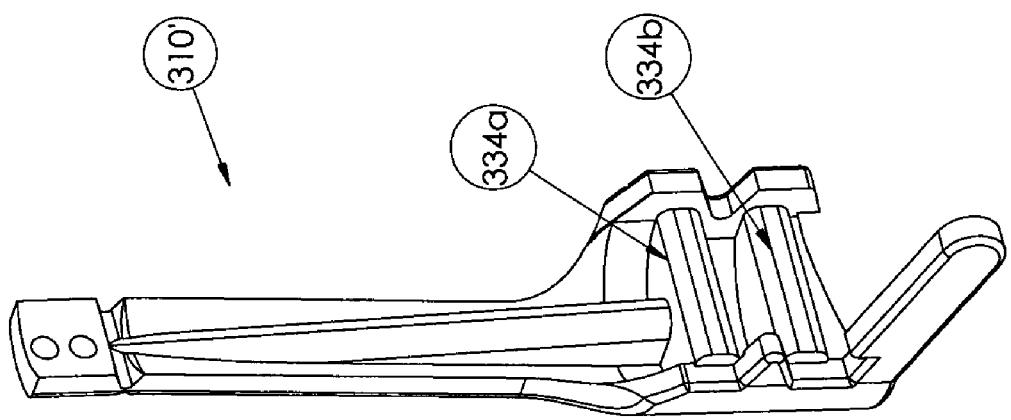
FIG. 10 is a perspective view of an alternative clamp segment of the catheter sheath clamp shown in FIG. 8.

The first and second clamping segments 310, 310' are now locked together, as shown in FIG. 8. The clamping member 334 of the first clamping segment 310 and the clamping member 334 of the second clamping segment 310' are brought toward each other, with the sheath 350 disposed between the two clamping members 334. The clamping members 334 pinch the sheath 350 closed, restricting fluid flow through the sheath 350. If the clamp 310' shown in FIG. 10 is used, the clamping member 334 is disposed generally between the clamping members 334*a* and 334*b*, also pinching the sheath 350 closed, restricting fluid flow through the sheath 350.

With the sheath 350 pinched closed, the physician now is able to attend to inserting the catheter 200 into the sheath 350 without the patient's blood flowing out of the sheath 350. The catheter 200 is inserted into the sheath 350 in a known manner, similar to the insertion of the catheter 200 into the sheath 100 as described above. When the catheter lumens 202, 204 are disposed within the sheath 350, as shown in FIG. 8, the lumens 202, 204 occlude passage of blood and/or air through the sheath 350.

To open the clamp 300, the physician grasps the clamp 300 with one hand. With the other hand, the physician holds the catheter for installation into the sheath 350. With the one hand, the physician places the thumb onto the top of the locking leg 328 of the first clamping segment 310 and the forefinger onto the top of the locking leg 328 of the second clamping segment 310' and biases both locking legs 328 downward, away from the tongue 324 of each respective clamping segment 310, 310'. The biasing action disengages the tang 332 on each of the clamping segments 310, 310' from the recessed portion 330 on each of the other clamping segments 310', 310. The first and second clamping segments 310, 310' are now unlocked from each other.

With the first and second clamping segments 310, 310' unlocked, the sheath 350 returns to its unpinched position, forcing the clamping members 334 away from each other so that fluid flow through the sheath 350 is unrestricted. With the other hand, the physician now fully inserts the catheter 200 into the sheath 350. After the catheter 200 is inserted into the vessel, the sheath 350 is torn from around the catheter 200 according to known techniques.

Figure 11:
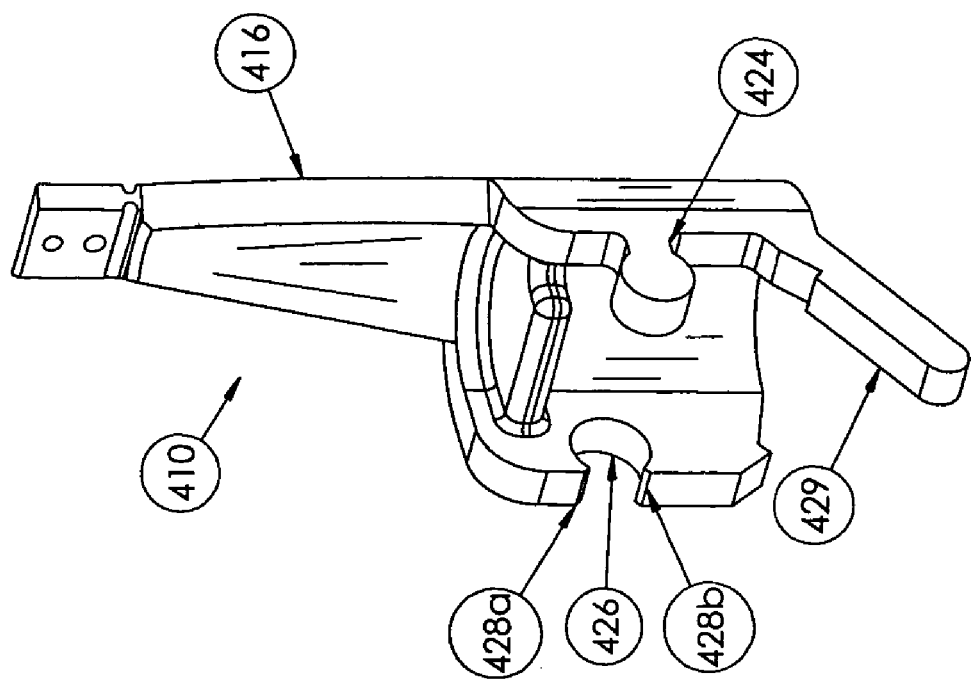
FIG. 11 is a perspective view of a catheter sheath clamp portion constructed in accordance with a third embodiment of the present invention.
Figure 12:
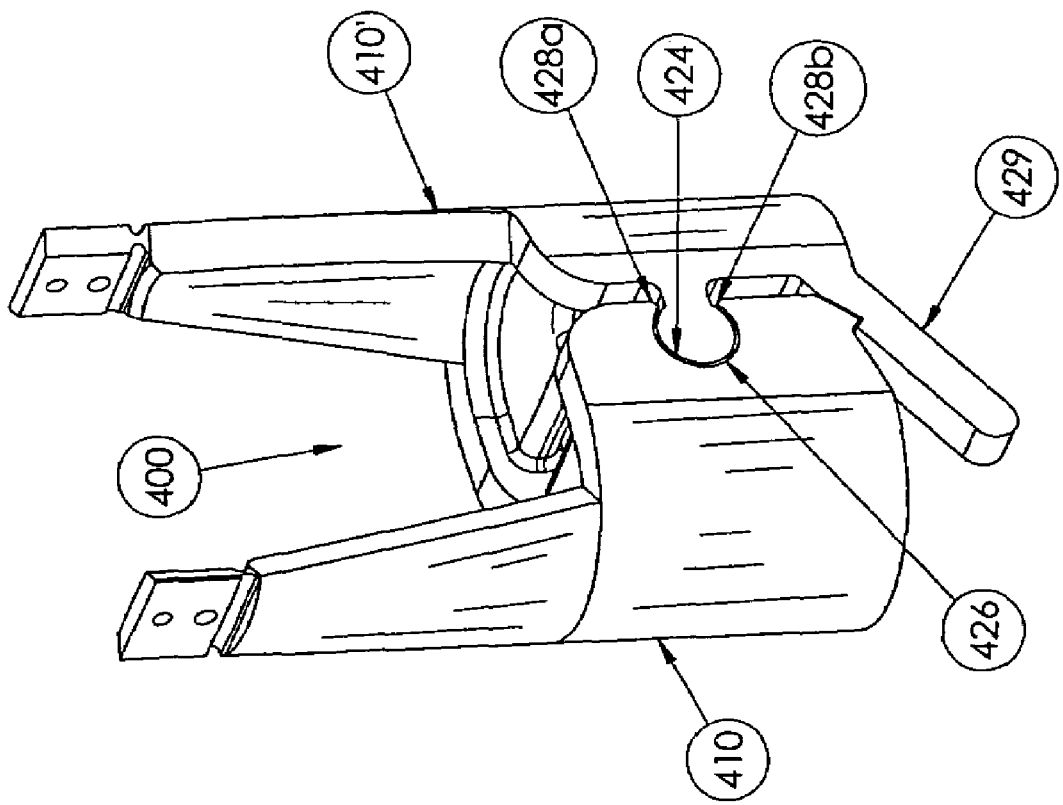
FIG. 12 is a perspective view of the catheter sheath clamp assembly using the clamp portion of FIG. 11, with the sheath omitted.

In an alternate embodiment of a clamp 400, shown in FIGS. 11 and 12, the generally triangular tongue 324 and mating groove 326 of the first clamping segment 310, 310' in the previous embodiment have been replaced by a clamping segment 410 having a generally bulbous tongue 424 and a complementary arcuate recess 426 that spans over 180 degrees of arc and that is sized to accept a tongue 424 from the second clamping segment 410'. The sheath 350 has been omitted for clarity. The recess 426 also preferably includes upper and lower beveled guide faces 428*a*, 428*b* to guide the tongue 424 from the one of the first and second clamping segments 410, 410' into the recess 426 of the other of the first and second clamping segments 410, 410'.

Although, as shown in FIGS. 11 and 12, the tongue 424 and the recess 426 have generally circular mating profiles, those skilled in the art will recognize that other profiles can be used, so long as the tongue 424 matingly engages with the recess 426.

To close the clamp 400, the physician places the thumb of one hand onto the body portion 416 of the first clamping segment 410 and biases the first clamping segment 410 toward the second clamping segment 410' and a finger of the same hand onto the body portion 416 of the second clamping segment 410' and biases the second clamping segment 410' toward the first clamping segment 410. The tongue 424 of the first clamping segment 410 engages the beveled guide faces 428*a*, 428*b* of the recess 426 of the second clamping segment 410', which guide the tongue 424 into the recess 426. Due to the flexible nature of the polymer material, the recess 426 expands proximate the beveled guide faces 428*a*, 428*b*, allowing the tongue 424 to fully engage the recess 426. After the tongue 424 is inserted into the recess 426, the recess 426 contracts or rebounds back to its original position, locking the tongue 424 within the recess 426. Simultaneously, the tongue 424 of the second clamping segment 410' engages the beveled guide faces 428*a*, 428*b* of the recess 426 of the first clamping segment 410, which guide the tongue 424 into the recess 426. The clamp 400 preferably clamps a sheath in the same manner as the clamp 300 described above.

The physician opens the clamp 400 in the same manner as described above with respect to the clamp 300. However, the physician must also exert a force on each locking leg 429 away from the sheath in order to expand the recess 426 proximate to the beveled guide faces 428*a*, 428*b* so that the tongue 424 can exit the recess 426. The catheter 200 is then inserted into the vessel as described above with respect to the clamp 300.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter insertion sheath comprising:
   a tubular sheath having a proximal end, a distal end, and a hollow passage extending between the proximal end and the distal end;
   a handle portion disposed at the proximal end of the tubular sheath; and
   a clamp assembly extending from the handle portion for releasably closing the sheath, the clamp assembly including at least one section in fixed relationship to the sheath adjacent thereto, and at least one section that is movable with respect to the fixed section and to the sheath, wherein the at least one movable section is translatable between an open position and a closed position, wherein, when in the open position, fluid may flow through the hollow passage between the proximal end and the distal end and when in the closed position, fluid flow is restricted through the hollow passage between the proximal end and the distal ends,
   wherein the clamp assembly is affixed to the handle and positioned adjacent to the sheath in such a manner that its at least one movable portion is operable with a single hand while that hand also holds the insertion sheath.

2. A catheter insertion sheath comprising:
   a flexible elongated body having a proximal end, a distal end, a longitudinal axis extending therethrough;
   a handle connected to the proximal end of the body; and
   a pinching assembly for pinching the body closed, wherein the pinching assembly extends from the handle, the pinching assembly including at least one section in fixed relationship to the sheath adjacent thereto, and at least one section that is movable with respect to the fixed portion and to the sheath, and wherein the at least one movable section is operable between an open position and a closed position.

3. The catheter insertion sheath according to claim 2, wherein the pinching assembly comprises a first portion disposed generally on one side of the longitudinal axis and a second portion, similar to the first portion, disposed generally on an opposing side of the longitudinal axis, wherein each of the first and second portions includes a fixed section and a movable section.

4. The catheter insertion sheath according to claim 3, wherein the first portion comprises a first tab and the second portion comprises a first recess, and wherein, when the pinching assembly is in the closed position, the first tab engages the first recess.

5. The catheter insertion sheath according to claim 4, further comprising the second portion having a second tab and the first portion having a second recess, and wherein, when the pinching assembly is in the closed position, the second tab engages the second recess.

6. The catheter insertion sheath according to claim 2, wherein the pinching assembly is hingedly connected to the handle.

7. The catheter insertion sheath according to claim 2, wherein the pinching assembly is operable with a single hand while that hand also holds the insertion sheath body.

8. The catheter insertion sheath according to claim 2, wherein the pinching assembly comprises:
   a body having a first end connected to the sheath handle and a second end having a slot extending through the body; and
   a generally planar unitary pinch member slidingly disposed within the slot between an open position and a pinching position, wherein the pinch member includes a first pinch leg having a first tapered free end and a first connected end and a second pinch leg juxtaposed from the first pinch leg, wherein the second pinch leg has a second tapered free end and a second connected end connected to the first connected end, and wherein the pinch member is slidable within the slot between a first position wherein the first and second tapered free ends are proximate to the slot and a second position wherein the first and second connected ends are proximate to the slot.

9. The catheter insertion sheath according to claim 8, wherein the body is generally elongated.

10. The catheter insertion sheath according to claim 8, wherein the first pinch leg comprises a first rib disposed toward the second pinch leg and wherein the second pinch leg comprises a second rib disposed toward the first pinch leg.

11. The catheter insertion sheath according to claim 8, wherein, when the first and second tapered free ends are proximate to the slot, the body is in an open position and when the first and second connected ends are proximate to the slot, the body is in a closed position.

12. A catheter insertion sheath assembly comprising:
   a catheter sheath including a generally tubular sheath body having a proximal end and a distal end;
   a handle fixedly connected to the proximal end of the sheath body; and
   a catheter sheath clamp comprising:
      a body having a first end connected to the sheath handle in a fixed relationship therewith and is adjacent the sheath and a second end having a slot extending through the body; and
      a generally planar pinch member slidingly disposed within the slot between an open position and a pinching position, wherein the pinch member includes a first pinch leg having a first tapered free end and a first connected end and a second pinch leg juxtaposed from the first pinch leg, wherein the second pinch leg has a second tapered free end and a second connected end connected to the first connected end, and wherein the pinch member is slidable within the slot between a first position wherein the first and second tapered free ends are proximate to the slot and a second position wherein the first and second connected ends are proximate to the slot.

13. The catheter insertion sheath assembly according to claim 12, wherein the body is generally elongated.

14. The catheter insertion sheath assembly according to claim 12, wherein the first pinch leg comprises a first rib disposed toward the second pinch leg and wherein the second pinch leg comprises a second rib disposed toward the first pinch leg.

* * * * *